United States Patent [19]

Hutchinson, Jr.

[11] Patent Number: 5,360,428

[45] Date of Patent: Nov. 1, 1994

[54] LAPAROSCOPIC INSTRUMENT WITH ELECTRICAL CUTTING WIRES

[76] Inventor: William B. Hutchinson, Jr., 1301 20th St. Suite 540, Santa Monica, Calif. 90404

[21] Appl. No.: 918,287

[22] Filed: Jul. 22, 1992

[51] Int. Cl.$^5$ ............................................. A61B 17/39
[52] U.S. Cl. ........................................ 606/45; 606/41; 606/46; 606/48
[58] Field of Search ............................ 606/41, 45–47, 606/52, 205, 208, 48–50

[56] References Cited

U.S. PATENT DOCUMENTS

| | | | |
|---|---|---|---|
| 2,004,559 | 6/1935 | Wappler et al. | 606/46 |
| 2,028,635 | 1/1936 | Wappler | 606/46 |
| 2,448,741 | 9/1948 | Scott et al. | 606/46 |
| 5,192,280 | 3/1993 | Parins | 606/50 |
| 5,201,732 | 4/1993 | Parins et al. | 606/47 |

OTHER PUBLICATIONS

Corson, Stephen M.D., "Two New Laparoscopic Instruments: Bipolar Sterilizing Forceps and Uterine Manipulator" Jan.–Feb. 1977 *Medical Instrumentation*, pp. 7–8.
ENDOlap Incorporated/American Rack & Pinion Catalog (pp. F–5a and F–35a, Ref. Spatula Electrode F265.02).
Multigon Industries, Inc. Laparoscopic Instruments and Supplies Catalog (pp. 10 and 11, Ref. Insulated Spatula Electrode Catalog No. 71.7240 and Dissecting Spatula Cannula, Catalog No. 735.5302).

*Primary Examiner*—Stephen C. Pellegrino
*Assistant Examiner*—M. Peffley
*Attorney, Agent, or Firm*—Lyon & Lyon

[57] ABSTRACT

A laparoscopic surgical cutting tool has a handle attached to a hollow tube. A tube end segment is pivotally attached to the tube. A linkage connects the handle to the end segment to allow the surgeon to adjust the angle between the end segment and tube, using the handle. A step projects upwardly at an angle at the distal end of the end segment. A lip attached to the end segment extends in a plane generally parallel to the axis of the end segment. Electrifiable cutting wires extend from an upper inside surface of the end segment to the lip.

7 Claims, 2 Drawing Sheets

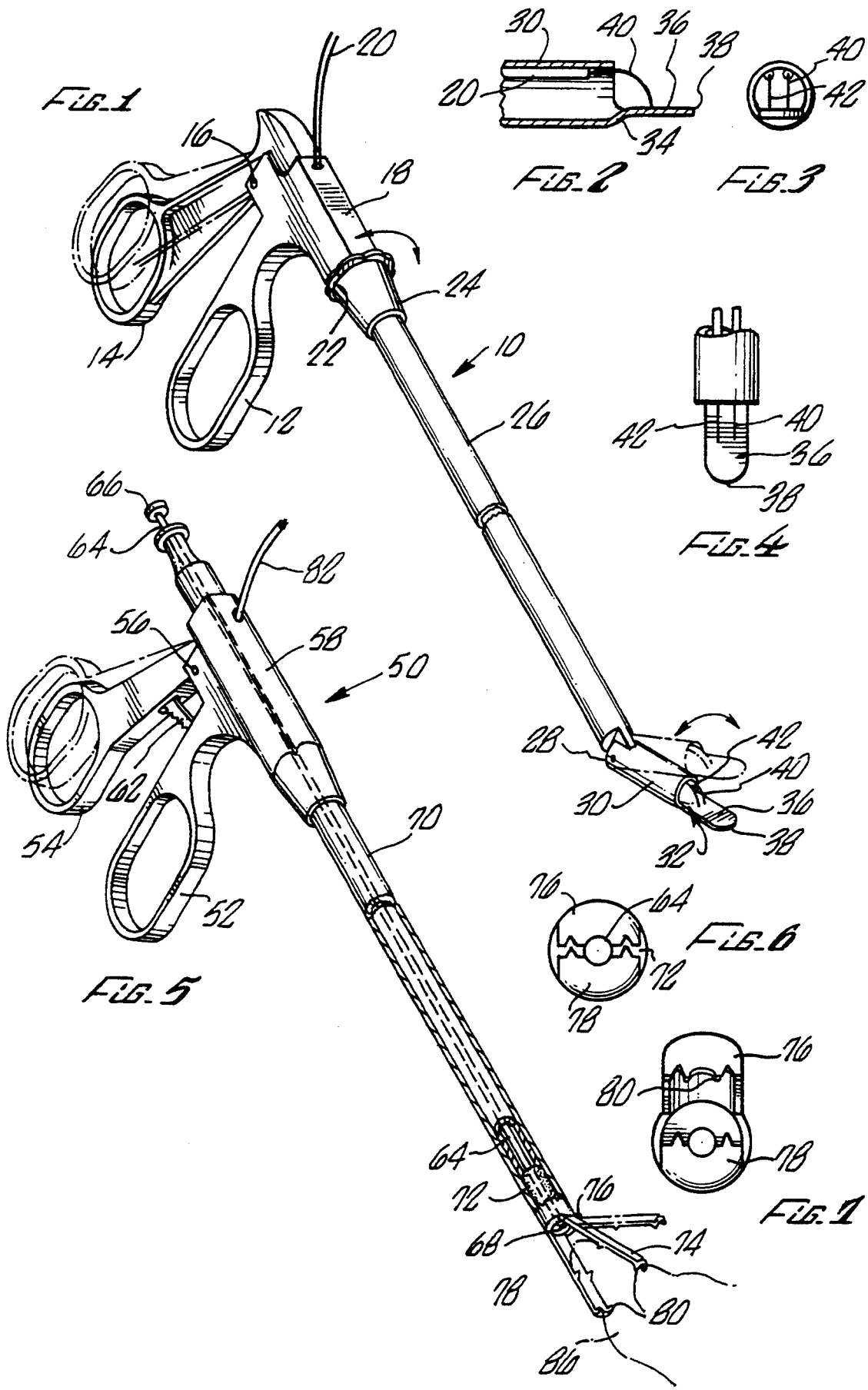

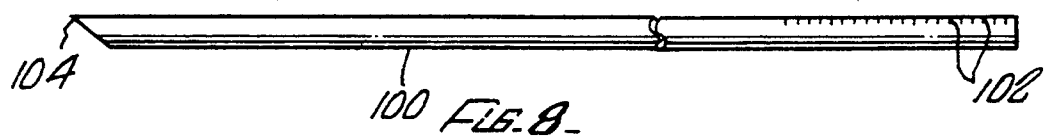
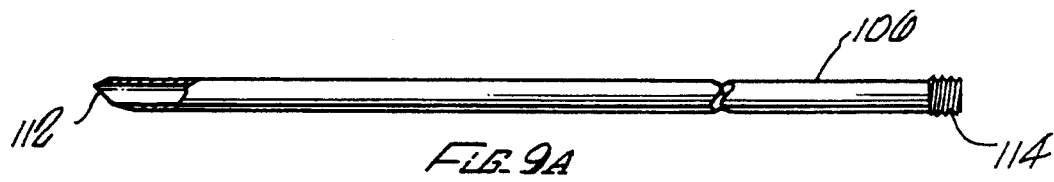
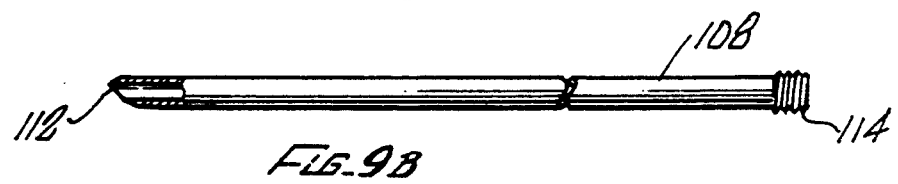
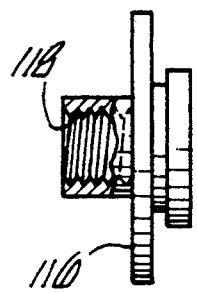
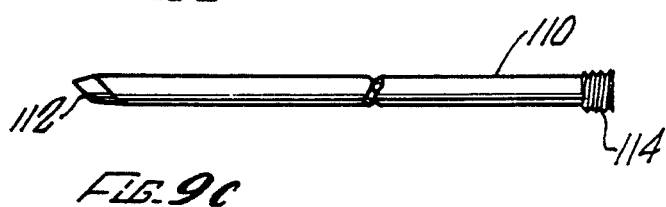
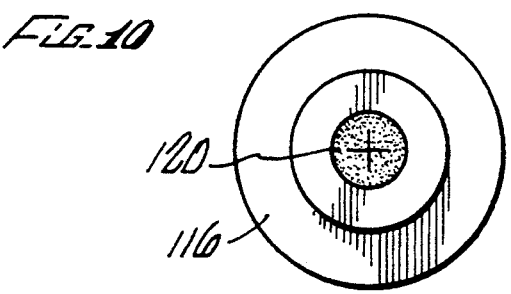
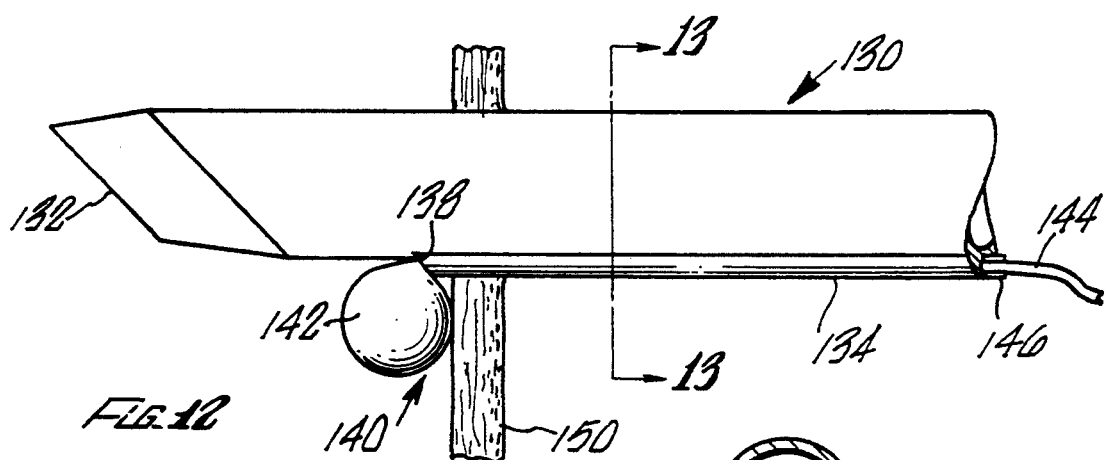
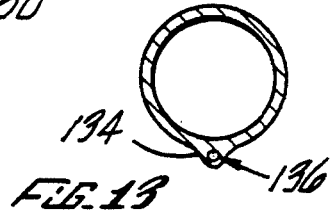

LAPAROSCOPIC INSTRUMENT WITH ELECTRICAL CUTTING WIRES

BACKGROUND OF THE INVENTION

The field of the invention is laparoscopic surgical tools.

Laparoscopic surgery is performed with laparoscopic tools extending through a relatively small incision in the patient. The surgeon manipulates the tool through handles or controls at the back of the tool remaining outside of the patient while a gripper, cutter, stapler, etc. at the front end of the tool within the patient performs surgical operations, while viewed by the surgeon via a miniature video camera placed within the patient. Laparoscopic surgery has several advantages over traditional surgery. Since only small incisions are made in the patient, the patient's hospital stay and recovery period are much shorter, and the patient's discomfort, pain and disability are significantly less than traditional surgery. Cosmetic disfigurement is also decreased. In addition, the surgical treatment itself and the overall entire cost of medical care for the procedure is less than with traditional surgery.

Typically, several incisions are made in the patient using trocars which provide ports or openings for the introduction of surgical tools, video camera, lights, and insufflation.

Various trocars, graspers, dissectors, and scissors have been used in performing laparoscopic surgery. However, in certain operations, cutting, grasping, and conveniently accessing the surgical site can be difficult.

SUMMARY OF THE INVENTION

The present invention is directed to improved laparoscopic tools. To this end, a laparoscopic tool has a pair of electrically conducting cutting elements extending from a lip. Also to this end, a laparoscopic tool has jaws for grabbing and holding an internal organ while it is pierced by a needle. A trocar is held in position with an inflatable balloon.

Accordingly, it is an object of the invention to provide improved laparoscopic tools.

BRIEF DESCRIPTION OF THE DRAWINGS

Other objects and features of the present invention will become apparent from the following detailed description taken in connection with the accompanying drawings. It is to be understood, however, that the drawings are designed for the purpose of illustration only and are not intended as a definition of the limits of the invention.

In the drawings, wherein similar reference characters denote similar elements throughout the several views:

FIG. 1 is a perspective view of the present laparoscopic tool;

FIG. 2 is a section view fragment of the front end of the tool of FIG. 1;

FIG. 3 is an end view thereof;

FIG. 4 is a plan view fragment thereof;

FIG. 5 is a perspective view, in part section, of another laparoscopic tool;

FIG. 6 is an end view thereof showing the jaws in a closed position;

FIG. 7 is an end view thereof showing the jaws in an open position;

FIG. 8 is a side elevation view of a needle for performing laparoscopic surgery;

FIGS. 9a, 9b and 9c are surgical access tubes for use with the needle of FIG. 8;

FIG. 10 is a side elevation view in part section of an end cap for use on the access tubes of FIGS. 9a, 9b and 9c;

FIG. 11 is a plan view of the end cap of FIG. 10;

FIG. 12 is a side elevation view fragment of an abdominal trocar; and

FIG. 13 is a section view taken along line 13—13 of FIG. 12.

DETAILED DESCRIPTION OF THE PREFERRED EMBODIMENTS

Turning now in detail to the drawings, as shown in FIG. 1, a laparoscopic cutting tool 10 has a front handle 12 and a pivoting handle 14 joined to the front handle 12 with a pin 16. The front handle 12 has a top frame 18. A tube 26 is rotatably attached to the top frame 18 of the front handle 12 through a collar 24 and racheted thumbwheel 22. The tube 26 can be made to any convenient length and is generally approximately 30 cm. The tube 26 is also hollow and has a round cross section, although other cross-sectional shapes, though not preferred, could be used. An end segment 30 is attached to the tube 26 through a pivot joint 28. A linkage of e.g., wires or rods, extends from the pivoting handle 14 through the tube 26 to the pivot joint 28 and end segment 30, to enable the end segment 30 to be pivoted by movement of the pivoting handle 14 as is well known in the art.

As shown in FIGS. 1-4, the end segment 30 has a front opening 32. A joggle or step 34 extends from the front (distal) end of the end segment 30 and supports a lip 36 having a rounded forward edge 38. The elevation of the lip 36 relative to the end segment 30 can be varied. Cutting wires 40 and 42 attached to the lip 36 extend concavely in a radius into the opening 32 and are joined with wires 20. Other wire configurations, e.g. convex or straight may also be used.

In use, the lip 36 is positioned by manipulating the tool 10, by squeezing and/or releasing the pivoting handle 14 to adjust the pivot angle between the end segment 30 and tube 26, and by adjusting the radial or sweep angle of the end segment 30 and lip 36 by turning the thumbwheel 22. An electric power source connected to the wires 20 electrifies the cutting wires 40 and 42 which then cut and cauterize as they are advanced through tissue.

In the prior art, in performing e.g., a gall bladder operation, the use of laparoscopic scissors requires cutting without guidance and typically results in a jagged cut. With the laparoscopic tool 10, on the other hand, the lip 36 allows tissue or lining to be lifted and then cut by the cutting wires, resulting in a smooth cut.

As shown in FIG. 5, a laparoscopic tool 50 has a pivoting handle 54 attached to a front handle 52 by a pin 56. A tube 70 is attached to a top frame 58 of the front handle 52. A rachet mechanism 62 holds the pivoting handle 54 in position. A fixed jaw 78 is attached to the front end of the tube 70 on the same side (i.e., the bottom) of the tube 70 as the front handle 52. A hinged jaw 74 is attached to the top of the front end of the tube 70, opposite the fixed jaw 78 with a hinge 76. The hinged jaw 74 and fixed jaw 78 have rounded grasping teeth 80, as shown in FIGS. 6 and 7. A cylindrical rubber seal 72 is positioned within the front end of the tube 70. The seal 72 has a central opening or through bore. A needle 64 has a shaft extending from a needle handle 66 through the tube 70 and the bore in the seal 72, with the point 68 of the needle generally flush with the leading end of the seal 72. The needle 64 has a central bore, as in a hypodermic syringe.

A mechanical linkage connects the hinged jaw 74 to the pivoting handle 54, to allow the pivoting handle 54 to control movement of the hinged jaw 74. An aspirator tube 82 extends through the top frame 58 of the front handle 52 and connects to a bore in the needle 64.

In use, the hinged jaw 74 is opened by opening the pivoting handle 54 or pulling it away from the front handle 52. The jaws 74 and 78 are placed around a gland or organ 86, e.g., a gall bladder. The teeth 80 on the jaws act to hold the organ 86 in position between the jaws, without cutting or piercing the organ 86.

With the organ 86 grasped by the jaws, the needle 64 is pushed forward and pierces the organ 86. The aspirator hose draws the liquid content of the gland, e.g., bile, out through the needle 64. A dye or other medium for performing, e.g., a cholangiogram, is then injected back through the aspirator hose 82 and needle 64 into the organ 86. The needle 64 is then withdrawn so that the point 68 is within or flush with the front of the seal 72, and the central bore in the needle is capped or sealed at the back end. The jaws preferably remain in position grasping the organ to squeeze the needle hole in organ closed and prevent leakage. Alternatively, the needle 64 can be withdrawn, the jaws released and the tool 50 removed or relocated.

As shown in FIGS. 8–11, a penetration needle 100 has a pointed end 104 and calibrations or length indications 102. Access tubes 106, 108 and 110 having lengths of e.g., approximately 25, 20 and 15 cm have pointed bevelled ends 112 and threads 114 at their back ends. An end cap 116 has threads 118 for engaging the threads 114 on the access tubes. A flap seal 120 is provided on the end cap 116.

In use, the penetration needle 100 is pushed through the patient's skin, with the end 104 positioned at the desired location within the patient. The length of the penetration needle 100 remaining outside of the patient is then noted using the length indications 102. Using this dimension, the appropriate length tube 106, 108 or 110 is selected and slid over the penetration needle 100 until the pointed bevelled 112 of the access tube reaches pointed end 104 of the penetration needle 100. The penetration needle 100 is withdrawn and the end cap 116 threaded onto the back end of the access tube. Other surgical tools and instruments, e.g., a cholangio catheter, can then be installed through the access tube.

Turning to FIGS. 12 and 13, an abdominal trocar 130 has a pointed bevelled end 132 and an extension 134, also having a pointed bevelled end 138. The trocar 130 attaches, e.g., with screw threads to a trocar head or handle. A bore 136 extends through the extension 134. An inflatable balloon 140 positioned at the bevelled end 138 of the extension 134 is connected to a supply tube 144. After the trocar 130 is inserted through the abdominal wall 150, the balloon 140 is inflated and holds the trocar 130 in position. Alternatively, the supply tube 144 can have an inflatable bulb end 142, with the supply tube 144 fed through the bore 136 so that the bulb portion 142 is pushed out of the bevelled end 138 and inflated after the trocar is in position. The supply tube 144 has a thickened cuff section 146 to prevent the supply tube from sliding forward in the bore 136, to enable the balloon to stay in position against the abdominal wall 150.

Thus, while several embodiments have been shown and described, it would be apparent to those skilled in the art that many more modifications are possible without departing from the inventive concepts. The invention, therefore, is not to be restricted except in the spirit of the appended claims.

I claim:

1. A laparoscopic cutting tool comprising:
   a substantially inflexible tube having a proximal end and a distal end;
   a handle attached to the proximal end of the tube;
   a generally flat lip extending from a lower surface of the distal end of the tube; and
   a pair of spaced apart electrically conducting cutting wires extending from an upper surface of the distal end of the tube to the lip; and
   means for providing electrical energy to the cutting wires.

2. The tool of claim 1 wherein the cutting wires extend concavely from the lip to the tube.

3. The tool of claim 1 wherein the tube is rotatably attached to the handle.

4. The tool of claim 1 further comprising a pivot joint dividing the tube into a handle segment and an end segment.

5. The laparoscopic tool of claim 1 wherein the cutting wires are fixed in position relative to the lip and distal end of the tube.

6. A laparoscopic cutting tool comprising:
   a tube having a proximal end and a distal end;
   a handle attached substantially perpendicular to the proximal end of the tube;
   a pivot segment having a front end and a back end with the back end of the pivot segment pivotally attached to the distal end of the tube;
   a pivot linkage mechanism coupled between the handle and the pivot segment for pivoting the pivot segment via the handle;
   a generally flat lip attached to the front end of the pivot segment;
   a pair of spaced apart electrically conducting cutting elements fixed in position relative to the lip and the front end of the pivot segment; and
   means for providing electric power to the cutting elements.

7. The laparoscopic tool of claim 6 wherein the cutting elements extend concavely in a radius between the lip and the pivot segment.

* * * * *